US00PP25342P2

(12) United States Plant Patent
Bunker

(10) Patent No.: US PP25,342 P2
(45) Date of Patent: Mar. 10, 2015

(54) ***BRACTEANTHA* PLANT NAMED 'FLOBRABLA'**

(50) Latin Name: *Bracteantha bracteata*
Varietal Denomination: Flobrabla

(71) Applicant: Kerry Veianne Bunker, Redland Bay (AU)

(72) Inventor: Kerry Veianne Bunker, Redland Bay (AU)

(73) Assignee: Floreta Intellectual Property Pty. Ltd., Redland Bay, NSW (AU), as Trustee for the Sundaze Beauty Trust ( * ) Notice: Subject to any disclaimer, the term of this patent is extended or adjusted under 35 U.S.C. 154(b) by 125 days.

(21) Appl. No.: 13/815,647

(22) Filed: Mar. 31, 2013

(51) Int. Cl.
*A01H 5/00* (2006.01)

(52) U.S. Cl.
USPC ..... Plt./359

(58) Field of Classification Search
USPC ..... Plt./263.1, 359
See application file for complete search history.

*Primary Examiner* — Susan McCormick Ewoldt
(74) *Attorney, Agent, or Firm* — C. A. Whealy

(57) ABSTRACT

A new and distinct cultivar of *Bracteantha* plant named 'Flobrabla', characterized by its upright, compact and uniformly rounded plant habit; freely branching habit; dense and bushy appearance; freely flowering habit; numerous inflorescences with showy golden yellow and rusty orange-colored involucral bracts; strong peduncles that hold the inflorescences above the foliar plane; and good garden performance.

1 Drawing Sheet

Botanical designation: *Bracteantha bracteata.*
Cultivar denomination: 'FLOBRABLA'.

BACKGROUND OF THE INVENTION

The present invention relates to a new and distinct plant of *Bracteantha* plant, botanically known as *Bracteantha bracteata*, and hereinafter referred to by the name 'Flobrabla'.

The new *Bracteantha* plant is a product of a planned breeding program conducted by the Inventor in Redland Bay, Queensland, Australia. The objective of the program is to create and develop new compact and freely flowering *Bracteantha* plants with attractive inflorescence coloration and good summer performance.

The new *Bracteantha* plant originated from a cross-pollination conducted by the Inventor in January, 2009 of a proprietary selection of *Bracteantha bracteata* identified as code number 09-022, not patented, as the female, or seed, parent with a proprietary selection of *Bracteantha bracteata* identified as code number 09-015, not patented, as the male, or pollen, parent. The new *Bracteantha* plant was discovered and selected by the Inventor as a single flowering plant from within the progeny of the stated cross-pollination in a controlled greenhouse environment in Redland Bay, Queensland, Australia in December, 2009.

Asexual reproduction of the new *Bracteantha* plant by vegetative cuttings in a controlled greenhouse environment in Redland Bay, Queensland, Australia since December, 2009 has shown that the unique features of this new *Bracteantha* plant are stable and reproduced true to type in successive generations.

SUMMARY OF THE INVENTION

Plants of the new *Bracteantha* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Flobrabla'. These characteristics in combination distinguish 'Flobrabla' as a new and distinct *Bracteantha* plant:

1. Upright, compact and uniformly rounded plant habit.
2. Freely branching habit; dense and bushy appearance.
3. Freely flowering habit.
4. Numerous inflorescences with showy golden yellow and rusty orange-colored involucral bracts.
5. Strong peduncles that hold the inflorescences above the foliar plane.
6. Good garden performance.

Plants of the new *Bracteantha* differ from plants of the female parent selection in the following characteristics:

1. Plants of the new *Bracteantha* have shorter leaves than plants of the female parent selection.
2. Inflorescences of plants of the new *Bracteantha* have fewer involucral bracts than inflorescences of plants of the female parent selection.
3. Involucral bracts of plants of the new *Bracteantha* are flatter than involucral bracts of plants of the female parent selection.
4. Involucral bracts of plants of the new *Bracteantha* and the female parent selection differ in color.

Plants of the new *Bracteantha* differ from plants of the male parent selection in the following characteristics:

1. Plants of the new *Bracteantha* have shorter and narrower leaves than plants of the male parent selection.
2. Inflorescences of plants of the new *Bracteantha* have fewer involucral bracts than inflorescences of plants of the male parent selection.
3. Involucral bracts of plants of the new *Bracteantha* are flatter than involucral bracts of plants of the male parent selection.

4. Involucral bracts of plants of the new *Bracteantha* and the male parent selection differ in color.

Plants of the new *Bracteantha* can be compared to plants of the *Bracteantha bracteata* 'Flobrafla', disclosed in U.S. Plant Pat. No. 16,950. In side-by-side comparisons conducted in Redland Bay, Queensland, Australia, plants of the new *Bracteantha* differed from plants of 'Flobrafla' in the following characteristics:

1. Plants of the new *Bracteantha* were not as dense as plants of 'Flobrafla'.
2. Plants of the new *Bracteantha* had narrower leaves than plants of 'Flobrafla'.
3. Inflorescences of plants of the new *Bracteantha* had more involucral bracts than inflorescences of plants of 'Flobrafla'.
4. Plants of the new *Bracteantha* and 'Flobrafla' differed in involucral bract color.

BRIEF DESCRIPTION OF THE PHOTOGRAPHS

The accompanying photographs illustrate the overall appearance of the new *Bracteantha* plant showing the colors as true as it is reasonably possible to obtain in colored reproductions of this type. Colors in the photographs may differ slightly from the color values cited in the detailed botanical description which accurately describe the colors of the new *Bracteantha* plant.

The photograph at the bottom of the sheet comprises a side perspective view of a typical flowering plant of 'Flobrabla' grown in a container.

The photograph at the top of the sheet is a close-up view of a typical flowering plant of 'Flobrabla'.

DETAILED BOTANICAL DESCRIPTION

The aforementioned photographs and following observations, measurements and values describe plants grown during the late autumn in one-gallon containers in an outdoor nursery in Bonsall, Calif. under cultural practices typical of commercial *Bracteantha* production. During the production of the plants, day temperatures ranged from 27° C. to 32° C., night temperatures ranged from 20° C. to 24° C. and light levels ranged from 6,000 to 8,000 foot-candles. Plants were three months old when the photographs and the description were taken. In the description, color references are made to The Royal Horticultural Society Colour Chart, 2007 Edition, except where general terms of ordinary dictionary significance are used.

Botanical classification: *Bracteantha bracteata* 'Flobrabla'.

Parentage:

*Female, or seed, parent*.—Proprietary selection of *Bracteantha bracteata* identified as code number 09-022, not patented.

*Male, or pollen, parent*.—Proprietary selection of *Bracteantha bracteata* identified as code number 09-015, not patented.

Propagation:

*Type*.—Vegetative cuttings.

*Time to initiate roots, summer*.—About three to four weeks at temperatures about 30° C.

*Time to initiate roots, winter*.—About four to five weeks at temperatures about 20° C.

*Time to produce a rooted young plant, summer*.—About eight weeks at temperatures about 30° C.

*Time to produce a rooted young plant, winter*.—About ten to twelve weeks at temperatures about 20° C.

*Root description*.—Fine, fibrous; pale brown in color.

*Rooting habit*.—Freely branching; medium density.

Plant description:

*Plant and growth habit*.—Upright, compact and uniformly rounded plant habit; dense and bushy appearance and inflorescences held above and beyond the foliar plane on strong peduncles; vigorous growth habit.

*Plant height*.—About 16.4 cm.

*Plant diameter or spread*.—About 37 cm.

*Lateral branches*.—Quantity per plant: Freely branching habit with about three primary branches each with about twelve lateral branches; pinching enhances lateral branch development. Length: About 16 cm. Diameter: About 6 mm. Internode length: About 1.3 cm. Aspect: Mostly upright to outwardly. Strength: Strong. Texture: Minute pubescence. Color: Close to 145B.

*Foliage description*.—Arrangement: Alternate, simple; sessile. Length: About 10.5 cm. Width: About 1.5 cm. Shape: Lanceolate to elliptic. Apex: Acute. Base: Truncate. Margin: Entire; slightly revolute. Texture, upper and lower surfaces: Minute pubescence. Venation pattern: Pinnate. Color: Developing leaves, upper surface: Close to 146C. Developing leaves, lower surface: Close to 146C to 146D. Fully expanded leaves, upper surface: Close to 147A; venation, close to 147C. Fully expanded leaves, lower surface: Close to 146A; venation, close to 147C.

Inflorescence description:

*Inflorescence type and flowering habit*.—Rotate composite inflorescence form; involucral bracts and disc florets developing acropetally on a capitulum; numerous inflorescences positioned mostly upright above and beyond the foliar plane on strong peduncles; terminal and axillary inflorescences face mostly upright; freely flowering habit with about 30 inflorescences developing per plant.

*Fragrance*.—Strong, sour scent.

*Time to flower*.—Plants begin flowering about three to six weeks after planting; flower continuously from late spring into the autumn in the California garden.

*Post-production longevity*.—Inflorescences maintain good substance for about one to two weeks on the plant; inflorescences persistent.

*Inflorescence buds*.—Height: About 1.7 cm. Diameter: About 1.2 cm. Shape: Roughly conical. Color: Close to 178A.

*Inflorescence diameter*.—About 4 cm.

*Inflorescence depth* (*height*).—About 2.7 cm.

*Disc diameter*.—About 1.7 cm.

*Receptacle height*.—About 1 cm.

*Receptacle diameter*.—About 1.8 cm.

*Involucral bracts*.—Length, largest bracts: About 1.4 cm. Width, largest bracts: About 4 mm. Shape: Elliptical. Apex: Acute. Base: Truncate. Margin: Entire. Texture, upper and lower surfaces: Smooth, glabrous; stiff, papery. Number of involucral bracts per inflorescence: About 116 arranged in about seven whorls. Color: When opening and fully opened, upper surface: Towards the apex, close to 172B; mid-section, close to N172B to N172C; towards the base, close to 23B. When opening and fully opened, lower surface: Close to N167C; towards the apex, close to 176A.

*Disc florets*.—Arrangement: Massed in the center of the receptacle. Shape: Slender tubular; apex dentate, five-pointed. Length: About 1.7 cm. Diameter: About 1 mm. Number of disc florets per inflorescence: About 700 in numerous tight whorls. Color, immature and mature: Towards the apex, close to 21B; mid-section, close to 1C; towards the base, close to 1D.

*Peduncles*.—Length, terminal peduncle: About 3.5 cm. Length, third peduncle: About 1.6 cm. Length, fifth peduncle: About 5 mm. Diameter, terminal peduncle: About 6 mm. Strength: Strong. Aspect: Upright to about 45° from lateral branch axis. Texture: Minute pubescence. Color: Close to 145A.

*Reproductive organs* (*present on disc florets only*).—Androecium: Arrangement: Fused anther tubes with five anthers surrounding the style. Filament length: About 8 mm. Filament color: Close to 145D. Anther length: About 2 mm. Anther color: Close to 21A. Pollen amount: Scarce. Pollen color: Close to 21A. Gynoecium: Pistil length: About 1.2 cm. Stigma shape: Bi-parted; reflexed. Stigma color: Close to 21C. Style length: About 9 mm. Style color: Close to 145D. Ovary color: Close to 157C.

*Seeds and fruits*.—Seed and fruit production has not been observed on plants of the new *Bracteantha*.

Disease & pest resistance: Plants of the new *Bracteantha* have not been shown to be resistant to pathogens and pests common to *Bracteantha* plants.

Garden performance: Plants of the new *Bracteantha* have been observed to have good garden performance and to tolerate rain, wind and temperatures ranging from about 4° C. to about 35° C.

It is claimed:

1. A new and distinct *Bracteantha* plant named 'Flobrabla' as illustrated and described.

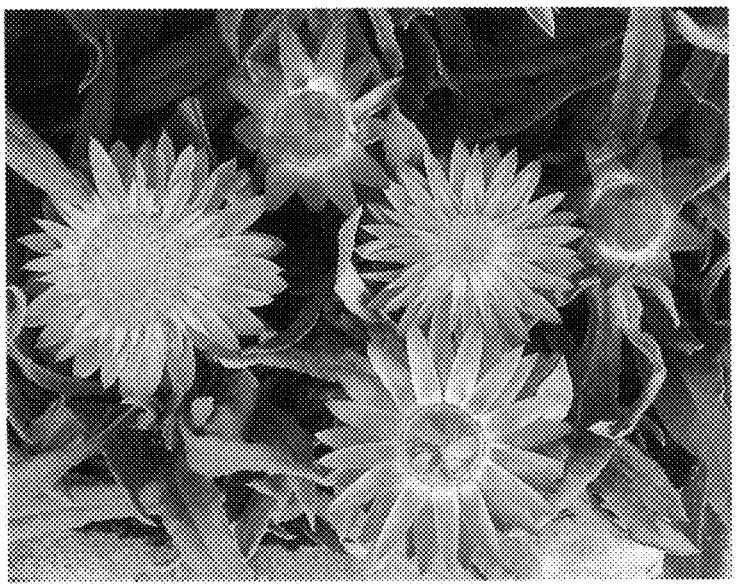
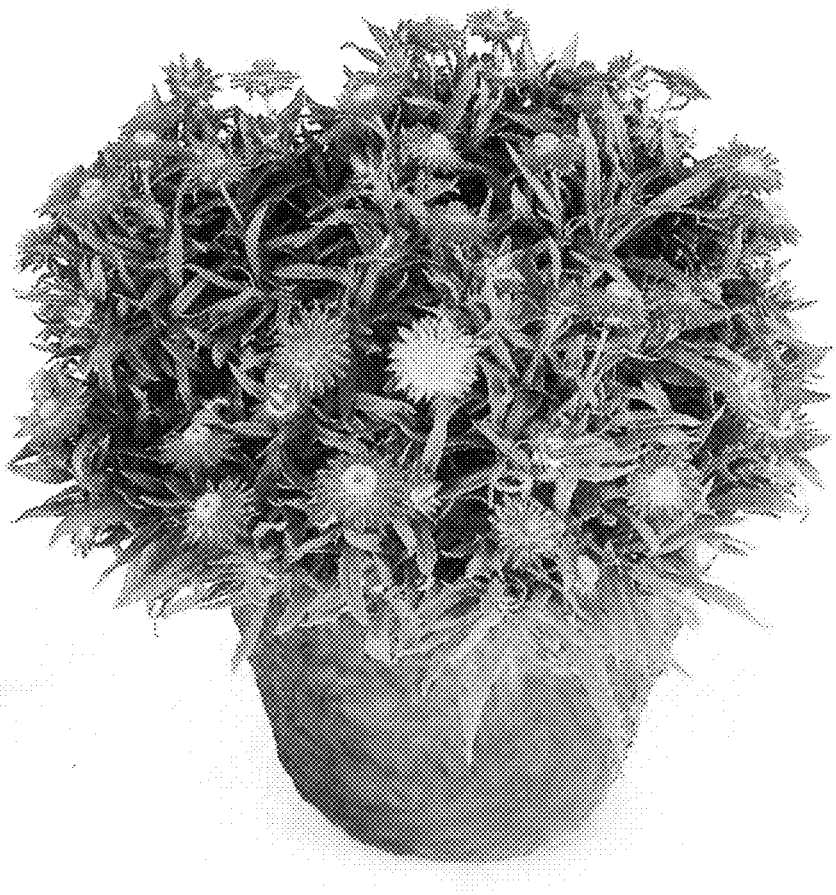

* * * * *